United States Patent [19]

Toja et al.

[11] Patent Number: 4,885,306
[45] Date of Patent: Dec. 5, 1989

[54] DERIVATIVES OF 1-ARYLSULPHONYL-2-OXO-5-ALKOXY-PYRROLIDINE AND MEDICAL COMPOSITIONS CONTAINING THEM

[75] Inventors: Emilio Toja; Carlo Gorini, both of Milan; Fernando Barzaghi; Giulio Galliani, both of Monza, all of Italy

[73] Assignee: Roussel Uclaf, Paris, France

[21] Appl. No.: 203,740

[22] Filed: Jun. 2, 1988

[30] Foreign Application Priority Data

Jun. 5, 1987 [IT] Italy ................................ 20809 A/87

[51] Int. Cl.$^4$ ..................... C07D 207/38; A61K 31/40
[52] U.S. Cl. ...................................... 514/425; 548/542
[58] Field of Search .......................... 548/542; 514/425

[56] References Cited

U.S. PATENT DOCUMENTS 3,117,975  1/1964  Bortnick et al. ..................... 548/545
3,423,426  1/1969  Kohn ................................... 548/542
3,686,169  8/1972  Coran et al. ......................... 548/542

FOREIGN PATENT DOCUMENTS 0138721  4/1985  European Pat. Off. .

OTHER PUBLICATIONS

Drugs of the Future, vol. 10, No. 12, 1985, pp. 972, 974.

Primary Examiner—David B. Springer
Attorney, Agent, or Firm—Stevens, Davis, Miller & Mosher

[57] ABSTRACT

Compounds useful in the treatment of patients suffering from intellectual or nervous asthenias, memory failures, senescence or mental strain of the formula (I)

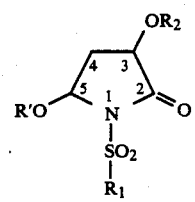

in which R' and $R_2$, being identical or different, represent hydrogen, a linear, branched or cyclic alkyl containing up to 8 carbon atoms, alkenyl containing from 2 to 8 carbon atoms, acyl containing from 1 to 6 carbon atoms or aralkyl containing from 7 to 15 carbon atoms, $R_1$ represents a possibly substituted aryl containing up to 14 carbon atoms, or a possibly substituted mono- or polycyclic heterocyclic aromatic radical; also therapeutic compositions containing those compounds and method of use.

10 Claims, No Drawings

DERIVATIVES OF 1-ARYLSULPHONYL-2-OXO-5-ALKOXY-PYRROLIDINE AND MEDICAL COMPOSITIONS CONTAINING THEM

The present invention relates to new derivatives of 1-arylsulphonyl-2-oxo-5-alkoxy pyrrolidine, the process for their preparation, their use as medicaments and compositions containing them.

The subject of the invention is the compounds with the general formula (I):

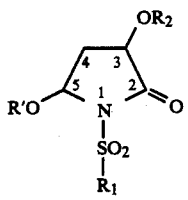

in which R' and $R_2$, being identical or different, represent hydrogen, linear, branched or cyclic alkyl containing up to 8 carbon atoms, alkenyl containing from 2 to 8 carbon atoms, acyl containing from 1 to 6 carbon atoms or aralkyl containing from 7 to 15 carbon atoms, $R_1$ represents aryl containing up to 14 carbon atoms, possibly substituted or a mono- or a polycyclic aromatic heterocyclic radical, possibly substituted.

The compounds with the formula (I) can exist in different diastereoisomeric forms, and the subject of the invention includes these different diastereoisomeric forms as well as their mixtures.

The preferred alkyl is an alkyl containing from 1 to 6 carbon atoms, for example, methyl, ethyl, n-propyl, isopropyl, n-butyl, isobutyl, tertbutyl, n-pentyl, n-hexyl, cyclopropyl, cyclobutyl, cyclopentyl or cyclohexyl.

The preferred alkenyl is ethenyl, propenyl or butenyl.

The preferred acyl is acetyl, propionyl or butyryl.

The preferred aralkyl is benzyl or phenethyl.

The preferred aryl is phenyl or naphthyl.

The preferred heterocyclic radical is thienyl, furyl, pyranyl, pyridyl, benzofuranyl, isobenzofuranyl, chromanyl, isochromanyl, chromenyl, xanthenyl, phenoxathienyl, oxazolyl, isoxazolyl, furazanyl, phenoxazinyl, thieno[2,3-b]furanyl, 2H-furo[3,2-b]pyranyl, benzoxazolyl or morpholinyl.

When $R_1$ is substituted, it is preferred for it to carry as substituents one or more substituents chosen from the group constituted by the free, esterified or etherified hydroxyl radical in which the ester or ether part contains from 1 to 18 carbon atoms, as for example, acetoxy, methoxy or benzyloxy, the ketone and oxime functions, the linear, branched or cyclic saturated or unsaturated alkyl radicals, containing up to 18 carbon atoms, for example, methyl, ethyl, propyl or isopropyl, ethenyl or ethynyl, halogen such as fluorine, chlorine, or bromine, the groups $CF_3$, $SCF_3$, $OCF_3$, $NO_2$, $NH_2$, or $C\equiv N$, phenyl and the alkylsulphonyl groups containing from 1 to 6 carbon atoms.

Among the preferred compounds of the invention, there can be cited the compounds with the formula (I) in which $R_2$ represents hydrogen, phenyl or a linear, branched or cyclic alkyl, containing up to 4 carbon atoms and quite particularly: 1-benzenesulphonyl-2-oxo-3-hydroxy-5-ethoxy pyrrolidine.

Also a subject of the invention is a process for the preparation of the compounds with formula (I), characterized in that a compound with the formula (II):

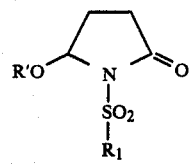

in which $R_1$ and R' retain their previous significance, is submitted to the action of hydroxylating agent, in order to obtain the corresponding compound with the formula $(I_A)$:

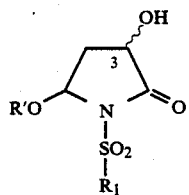

in the form of a mixture of isomers at position 3 which are separated, if desired, into each of the isomers, then, if desired, the mixture of isomers $(I_A)$ or each of its constituents is submitted to the action of an etherification or esterification agent in order to obtain the compound with the formula $(I_B)$:

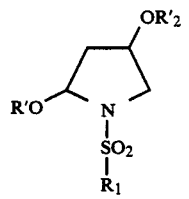

in which $R'_2$ has the values previously indicated for $R_2$, with the exception of a hydrogen atom, which compound with the formula $(I_B)$ is separated, if required, into each of its isomers.

In a preferred way of carrying out the invention process, the hydroxylation reagent is oxodiperoxymolibdenopyridine-hexamethyl phosphoramide or $MoO_5.Py.HMPA$ and the operation is done in the presence of lithium diisopropylamide in a mixture of tetrahydrofuran and hexane or 2-sulfonyloxaziridine and this is carried out in the presence of lithium bistrimethylsilylamide in a mixture of tetrahydrofuran and hexane.

The isomers at position 3 are separated by standard methods of chromatography and crystallization.

The etherification and esterification reactions are done by standard processes.

The invention compounds offer interesting pharmacological properties; they retard the extinction of the conditioned avoidance response, they retard the disappearance of the learned response. They favor attention, vigilance and memory.

The subject of the invention is therefore the compounds with the formula (I) as medicaments, useful notably in the treatment of intellectual or nervous asthenias, of memory failures, of senescence, and of mental strain.

More particularly, the subject of the invention as medicament is the compound of example 1.

The usual posology is variable according to the affection concerned, the subject treated and the administration route: the usual daily dose can be between 0.7 mg and 40 mg/kg and for example, between 2 mg and 20 mg/kg in one or more lots for the product of example 1, administered by oral route.

The subject of the present invention is also the pharmaceutical compositions containing, as the active principle, at least one compound of the formula (I).

The pharmaceutical compositions of the invention can be solid or liquid and are presented in the pharmaceutical forms currently used in human medicine, such, for example, as plain or sugar-coated tablets, capsules, suppositories and injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, and preservatives.

The products with the formula (II) used as starting products are products described and claimed in the European Patent filed on the 23rd of Dec. 1986 and published under the No. 0,229,566 on the 22nd of July 1987.

The following examples illustrate the invention without however limiting it.

EXAMPLE 1

1-benzenesulphonyl-2-oxo-3-hydroxy-5-ethoxy pyrrolidine

To 58 cm$^3$ of a solution of lithium diisopropylamide (0.68M) in hexane-THF (1-1), there is added at $-70°$ C. 4.83 of 5-ethoxyl-1-phenyl-sulphonyl-2-pyrroldine in solution in 100 cm$^3$ of tetrahydrofuran. The temperature is kept at $-70°$ C. for 15 minutes, then, in one lot, there is added at $-60°$ C. 11.68 g of the oxodiperoxymolybdenum pyridine hexamethyl phosphoramide complex MoOPH (MoOPH:oxodiperoxymolybdenum pyridine hexamethyl phosphotriamide:MoO$_5$.Py.HMPA prepared according to VEDEJS, ENGLER, TELSCHOW J. ORG. CHEM. (1978), 43, 188), maintained at $-50°$ C. for 2 hours then for 45 minutes at $-5°$ C. The reaction medium is decomposed by adding at $-45°$ C. a solution of sodium sulphite, and the medium is then salted out at 20° C. with 80 cm$^3$ of a saturated solution of sodium chloride. After extracting with chloroform, the extracts are dried and evaporated to dryness, then chromatographed on silica (eluent: hexane-ethyl acetate 1-3), and 0.74 g of a mixture of the 2 isomers is obtained, m.p. 80°-98° C.

Analysis: $C_{12}H_{15}NO_5S$. Calculated: C% 50.51; H% 5.30; N% 4.91; Found: C% 50.8; H% 5.27; N% 4.82.

One of the isomers is obtained by fractional crystallization from a mixture of isopropanol and isopropylether, m.p. 95°-97° C.

The second isomer is obtained by chromatography on silica (eluent hexane-ethyl acetate 1-2). m.p. 128°-130° C., recrystallized from isopropanol. HPLC analysis of the mixture has shown that the 2 isomers are in a ratio of 1 to 1 (column, 5 microns Lichrosorb Si 60 Merck 250 mm×4 mm mobile phase: tetrahydrofuran with 1% acetic acid-hexane 30-70. Elution 1 ml per minute. Injection 20 microliters, showing UV 260 nanometers).

As an alternative, and more advantageously, the two isomers can be separated by chromatography on a column "Lobar Lichroprep" Si 60 (Merck), elution with tetrahydrofuran with 1% acetic acid-hexane 30-70. The isomer which melts at 128°-130° C. has an Rf. of 0.16 and the isomer which melts at 95°-97° C. has an Rf. of 0.11.

Preparation of 1-benzenesulphonyl-2-oxo-5-ethoxy pyrrolidone

To 45 g of 5-ethoxy pyrrolidine-2-one in solution in 140 cm$^3$ of tetrahydrofuran, there is added 21.8 cm$^3$ of a 1.6M solution of butyllithium in hexane cooled to $-10°$ C. After 45 minutes, 6.15 g of benzenesulphonyl chloride in tetrahydrofuran is added, and the whole is maintained at $-10°$ C. for 2 hours, then concentrated under reduced pressure, and taken up with ethanol. The product is isolated by filtering, and 2.8 g of the expected product is obtained. m.p. 112°-113° C., crystallized from isopropanol.

Analysis: Calculated: C% 53.52; H% 5.61; N% 5.20; Found: C% 53.30; H% 5.64; N% 5.10.

EXAMPLE 2

1-benzenesulfonyl-2-oxo-3-hydroxy-5-ethoxypyrrolidine

To a solution of 10 g of 5-ethoxy-1-benzenesulfonyl-pyrrolidin-2-one in 300 cm$^3$ of anhydrous tetrahydrofuran, cooled to $-78°$ C., 0.037 moles of a solution of lithium bis-trimethylsylylamide in a mixture of hexane-tetrahydrofuran (1-1) is added drop by drop at a temperature of $-78°$ C. This mixture is agitated for 1 hour at $-78°$ C., then 14.55 g of 2-sulfonyloxaziridine is added. The mixture is then agitated at $-78°$ C. for 2 hours, brought to $-5°$ C., then cooled to $-30°$ C., after which 130 cm$^3$ of an aqueous solution of saturated ammonium chloride is added, while the temperature is maintained at approximately $-30°$ C. The temperature is brought to 20° C., then 130 cm$^3$ of an aqueous solution of saturated sodium chloride is added. The organic phase is separated and the aqueous phase is extracted with chloroform. The organic phases are combined, dried, and the solvent is evaporated under reduced pressure, then the residue is chromatographed on silica, using an ethyl acetate-hexane (2-1) mixture as eluent. The product is dissolved in isopropyl ether, and 250 g of the expected product is obtained, m.p. 108°-116° C. (mixture of cis and trans isomers in which the trans isomer predominates).

EXAMPLE 3

1-benzenesulfonyl-2-oxo-3-hydroxy-5-isopropyloxypyrrolidine

To a solution of 3.00 g of 1-benzenesulfonyl-5-isopropyloxy-2-pyrrolidine (described in European patent application No. 299,566) in 60 cm$^3$ of anhydrous tetrahydrofuran, cooled to $-78°$ C., under nitrogen, 36.39 cm$^3$ of a solution of 0.64 Mi lithiumdiisopropyl amide in a mixture of tetrahydrofuran-hexane (1-1) is added drop by drop, while maintaining the whole at $-78°$ C. After the mixture is agitated for 45 minutes at $-78°$ C., 6.90 g of oxodiperoxymolybdenum pyridine hexamethylphosphorotriamide is added, while keeping the whole at $-78°$ C. The temperature of the mixture is brought to $-5°$ C., then cooled to $-50°$ C. and agitated for 1 hour, then at −18° C. for 2 hours. The mixture is cooled to approximately −50° C. and 50 cm³ of an aqueous solution of saturated ammonium chloride is added drop by drop. The mixture is brought to room temperature and 50 cm³ of an aqueous solution of saturated sodium chloride is added drop by drop. The organic phase is separated and the aqueous phase is extracted with chloroform. The organic phases are combined and washed with 2N hydrochloric acid. After drying and removal of the solvent under reduced pressure, the residue is chromatographed on silica by elution with a mixture of ethyl acetate-hexane (1-1). After recrystallization in isopropanol, 0.40 g of a white solid is obtained, m.p. 127°–129° C. (trans isomer).

Analysis: $C_{13}H_{17}NO_5S = 299.35$. Calculated: C% 52.16; H% 5.72; N% 4.68; Found: 52.35; H% 5.65; N% 4.61.

EXAMPLE 4

1-benzenesulfonyl-2-oxo-3-ethoxy-5-ethoxypyrrolidine

To a mixture formed by 1 of 1-benzenesulfonyl-2-oxo-3-hydroxy-5-ethoxypyrrolidine (trans isomer), 30 cm³ anhydrous methylene chloride, and a small amount of aluminum chloride, at −10° C. 5 cm³ of diazoethane is added drop by drop. A small amount of aluminum chloride (a catalytic amount) is added, as well as approximately 6 cm³ of diazoethane, also at −10° C. After one hour, the mixture is brought to room temperature, washed with 10 cm³ of 1% acetic acid, then with 5% NaHCl₃, dried, evaporated to dryness under reduced pressure and chromatographed on silica by eluting with an ethyl acetate-hexane mixture (1-1) and 0.17 g of the expected product is obtained.

Analysis: $C_{14}N_{19}NO_5S = 313.376$. Calculated: C% 53.66; H% 6.11; N% 4.47; Found: C% 53.92; H% 5.97; N% 4.34.

EXAMPLE 5

1-benzenesulfonyl-2-oxo-3-acetoxy-5-ethoxy-pyrrolidine

A solution of 0.50 g of 1-benzenesulfonyl-2-oxo-3-hydroxy-5-ethoxypyrrolidine (trans isomer) in 10 cm³ anhydrous acetic acid is heated to boiling for 1 hour. It is allowed to cool to room temperature and the acetic anhydride is evaporated. It is dissolved in toluene and the azeotrope is evaporated under reduced pressure. The residue is chromatographed on silica by elution with a mixture of ethylacetate-hexane (1-1); 0.48 g of the expected product is obtained.

EXAMPLE 6

Pharmaceutical compositions (a) Tablets answering to the following formula have been prepared:
Product of example 1 ( mixture of isomers)—100 mg
Excipient q.s. for a table finished at—300 mg
(detail of excipient: lactose, corn starch, treated starch, rice starch, magnesium stearate, talc).

(b) Capsules answering to the following formula have been prepared:
Product of example 1 (mixture of isomers)—200 mg
Excipient q.s. for a tablet finished at—300 mg
(detail of excipient, talc, magnesium stearate, aerosil).

PHARMACOLOGICAL STUDY

Acute toxicity and behavior of the invention products

There were used male mice ($CD_1$ Charles Rivers) weighing 22–23 g, without food for 16 hours. The products were administered to them normally by oral route at doses at 1000–500–250 mg/kg.

The effect of the products on the behavior of the animals was evaluated according to the method described by Irvin (Psychopharmacology (1968), 13, 222–257) during the first 8 hours and on the 24th hour.

The mortality was noted during the 7 days following the treatment.

The $LD_{50}$ was thus found to be greater than 1000 mg/kg.

Learning and Memorizing

There were used male mice ($CD_1$ Charles Rivers) weighing 25–30 g. The animals were placed in the illuminated part of a box with two compartments communicating by an opening (G. Galliani, R. Cesana and F. Barzaghi, Med. Sci. Res. (1987), 15, 313–314).

At the instant when the mouse passes from the illuminated compartment to the dark compartment the opening closes and the mouse is immediately punished by an electric discharge to the paws. The animal submitted to this procedure learns to remember the punishment. In fact, if it is put back in the illuminated compartment, it will avoid crossing the opening and returning to the dark compartment.

In order to induce a retrograde amnesia, the animals are submitted immediately after the learning to an electric shock. After the electric shock, the products are administered by oral route at doses of 12.5; 25; 50; 100 and 200 mg/kg.

There were used 10 to 50 animals per dose.

The anti-amnesic effect of the products is evaluated 3 hours after the treatment, by using the same procedure as that utilized for the acquisition.

The time taken by the animal to return to the dark chamber (time limit 180 seconds) is used as evaluation parameter.

Under the same experimental conditions, the control animals enter with a time lapse of 40–50 seconds.

The active products are those which cause a significant increase in the latency time.

The results are expressed in percentages of increase of the latency times by comparison with the corresponding controls. Results obtained are provided with two reference products.

The following Table shows the results:

| PERCENTAGE INCREASE IN LATENCY TIME IN COMPARISON WITH THE CONTROLS | | | | |
|---|---|---|---|---|
| | Dose mg/kg per os | | | |
| | 200 | 100 | 50 | 25 |
| Product of example 1 (mixture) | 103* | 84* | 65* | 21 |
| Isomer m.p. 128–130° C. | 110* | 106* | 52* | 22 |
| Isomer m.p. 95–97° C. | 121* | 112 | 63* | 38 |
| PIRACETAM | 20 | 48* | 10 | 19 |
| ANIRACETAM | 32 | 88* | 77* | 39 |

*Values statistically different as compared with the controls.

Conclusion:

The product of example 1 and its isomers have shown an important anti-amnesic activity at doses between 50

What is claimed is:

1. Compounds with the general formula (I):

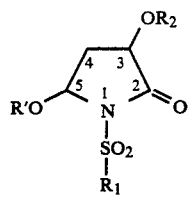

in which R' represents hydrogen, or alkyl containing up to 8 carbon atoms, $R_1$ represents phenyl possibly substituted by one or more substituents selected from the group consisting of a free, esterified or etherified hydroxyl radical in which the ester or ether part contains from 1 to 18 carbon atoms, the ketone and oxime functions, a linear, branched or cyclic, alkyl or alkenyl, having up to 18 carbon atoms, halogen, $CF_3$, $SCF_3$, $OCF_3$, $NO_2$, $NH_2$, C≡N, phenyl and alkylsulphonyl having from 1 to 6 carbon atoms, and $R_2$ represents hydrogen or linear, branched or cyclic alkyl containing up to 4 carbon atoms.

2. The compounds of the formula (I) as defined in claim 1 in which $R_2$ represents hydrogen.

3. The compounds of the formula (I) as defined in claim 1 or 2, in which $R_1$ represents phenyl.

4. The compounds of the formula (I) as defined in claims 1 or 2, in which R' represents a linear, branched or cyclic alkyl containing up to 4 carbon atoms.

5. The compounds of the formula (I) as defined in claim 3, in which R' represents a linear, branched or cyclic alkyl containing up to 4 carbon atoms.

6. A compound as defined in claim 1, which is 1-benzenesulphonyl-2-oxo-3-hydroxy-5-ethoxy pyrrolidine.

7. A therapeutic composition comprising a therapeutically effective amount of a compound as defined in any one of claims 1, 2, or 5, and a pharmaceutically acceptable carrier.

8. A therapeutic composition comprising a therapeutically effective amount of a compound as defined in claim 3, and a pharmaceutically acceptable carrier.

9. A therapeutic composition comprising a therapeutically effective amount of a compound as defined in claim 4, and a pharmaceutically acceptable carrier.

10. A therapeutic composition comprising a therapeutically effective amount of a compound as defined in claim 6, and a pharmaceutically acceptable carrier.

* * * * *